United States Patent [19]

Schomberg et al.

[11] 4,279,157
[45] Jul. 21, 1981

[54] METHOD OF AND DEVICE FOR DETERMINING THE INTERNAL STRUCTURE OF A BODY BY MEANS OF ACOUSTIC BEAMS

[75] Inventors: Hermann Schomberg, Hamburg; Manfred Tasto, Henstedt-Ulzburg, both of Fed. Rep. of Germany

[73] Assignee: U.S. Philips Corporation, New York, N.Y.

[21] Appl. No.: 45,900

[22] Filed: Jun. 6, 1979

[30] Foreign Application Priority Data

Jun. 22, 1978 [DE] Fed. Rep. of Germany ....... 2827423

[51] Int. Cl.$^3$ ............................................. G01N 29/00
[52] U.S. Cl. ...................................... 73/618; 73/626; 128/660
[58] Field of Search ................. 73/597, 599, 618, 620, 73/626, 606, 607; 128/660

[56] References Cited

U.S. PATENT DOCUMENTS

| | | | |
|---|---|---|---|
| 4,058,001 | 11/1977 | Waxman | 73/620 |
| 4,075,883 | 2/1978 | Glover | 73/618 |
| 4,105,018 | 8/1978 | Greenleaf et al. | 73/597 |
| 4,222,274 | 9/1980 | Johnson | 73/626 |

FOREIGN PATENT DOCUMENTS

1448471 9/1976 United Kingdom .

*Primary Examiner*—Stephen A. Kreitman
*Attorney, Agent, or Firm*—Thomas A. Briody; Robert T. Mayer; Jack E. Haken

[57] ABSTRACT

A method and device for determining the internal structure of a body by means of acoustic beams. Transit times and intensities of acoustic beams passing through the body in different spatial directions are measured to establish the refractive index distribution and the acoustic absorption coefficient distribution, respectively at the points of a point matrix associated with the body. The non-rectilinear course of the acoustic beams is taken into account in this respect. This results in reconstructed images of higher quality.

17 Claims, 11 Drawing Figures

METHOD OF AND DEVICE FOR DETERMINING THE INTERNAL STRUCTURE OF A BODY BY MEANS OF ACOUSTIC BEAMS

The invention relates to a method and a device for performing the method of determining the internal structure of a body by means of acoustic beams which extend between separate acoustic transmission elements and acoustic receive elements of an acoustic converter which at least partly encloses the body. The acoustic receive elements are struck by acoustic beams which pass through the body in different directions. The transit times of the acoustic beams is used to determine the acoustic refractive index at individual points of a point matrix associated with the body.

A method of this kind is already known from German Offenlegungsschrift No. 27 37 109. Using a receiver/converter in the form of an arc of a circle and an altrasonic fan-shaped beam which passes through a body to be examined from different directions which are situated in one plane, transit time projections of the acoustic signals are obtained for each direction, the combination of said transit time projections enabling the reconstruction of a velocity distribution at known coordinates in a layer of the body. In this respect it is assumed that the ultrasonic pulse passing through the body follows an approximately rectilinear, known path, so that for the reconstruction use can be made of reconstruction methods such as used for the reconstruction of X-ray tomography images (J. F. Greenleaf c.s., "Acoustical Holography", Plenum Press, Vol. 6, pages 71–89, 1975).

The path of the acoustic signals (acoustic beams), however, is dependent of the distribution of the acoustic refractive indices within the body to be examined, the acoustic beams usually not being rectilinear, so that reconstruction methods of this kind can be used to only a limited extent for the formation of high-quality reconstruction images.

The invention has for its object to provide a method which enables the reconstruction of higher quality acoustic images of internal body structures.

To this end, the method in accordance with the invention is characterized in that from a distribution of the acoustic refractive indices which is preselected at the points of the point matrix and which approximates the structure of the body, taking into account the geometry of the acoustic converter, the path through the body is calculated at least once for each acoustic beam, the transit time of the beam being calculated therefrom, the measured and the calculated transit time of an acoustic beam being used to determine correction data for the step-wise correction of the values of the acoustic refractive indices at the points of the point matrix.

This method enables the determination of a correct structure distribution in given areas, for example, of the human body. The method is notably suitable for examinations of the mammae for detection and diagnosis of cancer of the breast as well as for the testing of material. The acoustic refractive index of the body to be examined is determined at individual points of a point matrix which is permanently associated therewith. The individual values of the acoustic refractive indices can then be converted, for example, into corresponding gray values for the reproduction of individual layer images which can be displayed on a screen or printed by a printer.

A preferred method in accordance with the invention utilizes acoustic beams which extend in different directions in order to determine a spatial structure distribution of a three-dimensional body.

It is thus achieved that a single exposure of a patient suffices, for example, to determine the acoustic refractive index distribution in a three-dimensional zone of the body of the patient. Using electronic means, individual layers which extend through the point matrix permanently associated with the body can then be made visible on a monitor. The layers need not necessarily be flat.

Another method in accordance with the invention is characterized in that the intensity of the individual acoustic beams is also measured by means of the acoustic receive elements, the transmission intensity being determined in the direction of the path of each acoustic beam, taking into account the path of the acoustic beams and the transmission characteristic of the acoustic transmission elements. The transmission intensity is used to obtain an absorption signal which is characteristic of the absorption of the acoustic beam, the total absorption along the acoustic beam path being consecutively determined at least once for all acoustic beams from a distribution of the absorption coefficients which is preselected at the points of the three-dimensional point matrix and which approximates the structure of the body. Correction values are obtained for the step-wise correction of the absorption coefficient at the points of the point matrix by comparison of the total absorption with the absorption signals measured.

The distribution of the absorption coefficients can be determined only after the course of the acoustic beam paths is known (for example, from the preceding acoustic refractive index reconstruction). If, moreover, the transmission characteristic of the acoustic transmission is known, the intensity transmitted by these elements in the direction of the acoustic beam paths can be calculated. It is thus achieved, that in addition to the refractive index distribution, the distribution of the absorption coefficients is available for a more accurate diagnosis of the internal structure of a body. The transmission characteristic of the individual acoustic transmission elements is known or can be determined prior to the start of the measurements.

A further embodiment of the invention is characterized in that the direction of the acoustic beams is changed by activation of separate acoustic transmission elements and acoustic receive elements of the acoustic converter which are arranged around the body, the position thereof remaining unchanged with respect to the body surrounded by an acoustic coupling medium.

It is thus achieved that the acoustic converter need no longer be rotated around the body to be examined or only partly so. The time required for measuring the transit times of the acoustic beams or the intensities is thus substantially reduced. It will be clear that, also during rotary scanning of the object, the axis of rotation may not be shifted with respect to the body, because otherwise correct image reconstruction is not possible.

A device in accordance with the invention is characterized in that there is provided a first memory section for the storage of the transit times measured, a second memory section for the storage of previously selected values, or values adapted on the basis of measuring results, of the refractive indices at the matrix points, a third memory section for the storage of calculated values of the transit times, and a fourth memory section for the storage of further data, there also being provided a central processor unit which is adapted to calculate the transit times from the distribution of the acoustic refractive indices, to calculate correction data from the measured transit times and the calculated transit times, and to calculate corrected values of the refractive indices on the basis thereof.

A further embodiment of the device in accordance with the invention is characterized in that there is provided a fifth memory section for the storage of the intensities of the acoustic beams received and of the associated transmitted acoustic beam, a sixth memory section for the storage of the measured absorption signal determined therefrom, a seventh memory section for the storage of preselected values, or values adapted on the basis of measuring results, of the absorption coefficients at the matrix points, and an eight memory section for the storage of the calculated absorption along each of the acoustic beam paths. The central processor unit is further adapted to calculate the measured absorption signals from the transmitted and the received intensities, to calculate the values of the calculated absorption from the distribution of the absorption coefficients, to calculate correction values from the measured and the calculated absorption values, and to calculate corrected values of the absorption coefficients on the basis thereof.

The device preferably comprises a tank which is rotatable around an axis of rotation, which is displaceable in the direction of the axis of rotation and which can be filled with an acoustic coupling medium prior to the introduction of the body to be examined.

The level of the rotatable tank, accommodating a two-dimensional acoustic converter, can be adjusted or its position with respect to the body can be rotated around an axis of rotation by means of motors.

Obviously, the acoustic transmission elements can also be used as acoustic receivers and vice versa, so that in a position of the acoustic converter each time two measurements shifted through 180° can be performed, with the result that the overall measuring time is substantially reduced.

In another embodiment yet of the device in accordance with the invention, the acoustic converter consists of a flat acoustic transmission matrix and a flat acoustic receive matrix which are composed of separate, suitably activatable acoustic transmission elements and acoustic receive elements, respectively, the matrix columns and matrix rows extending parallel and perpendicularly, respectively, to the axis of rotation.

A matrix row of acoustic transmission elements is each time situated opposite a row of acoustic receive elements in a plane perpendicular to the axis of rotation. These rows are mutually parallel and rotatable around this axis of rotation. In each angular position, pairs of acoustic transmission matrix rows and acoustic receive matrix rows which are situated one above the other in the direction of the axis of rotation are successively activated by the successive activation of each time oppositely situated, separate acoustic transmission elements and acoustic receive elements, respectively, of a matrix row. The body is thus layer-wise scanned.

The tank accommodating the acoustic converter need not be displaced in the direction of the axis of rotation. The examinations are thus substantially facilitated and reduced. Obviously, several or all acoustic receive elements of an acoustic receive matrix can be simultaneously activated when an acoustic transmission element of the oppositely situated acoustic transmission matrix row is activated. The information density is thus increased, so that the image reconstruction is improved.

In a further preferred embodiment of the invention, the acoustic transmission matrix consists of a single plate-like acoustic transmitter.

It is thus achieved that the acoustic waves transmitted by the acoustic transmitter are almost flat, so that the starting direction of the acoustic beams which extend perpendicularly to the acoustic wave fronts and which reach the acoustic receive matrix is at least approximately predetermined. Moreoever, the activation of the acoustic transmission matrix is substantially simplified, because no electronic device is required for activating given, individual acoustic transmission elements. Because the wave fronts of the acoustic waves arrive at a given angle with respect to the acoustic receive matrix, the arrival direction thereof can at least be approximately determined by the transit time differences of the acoustic beams. In a further preferred embodiment in accordance with the invention, the acoustic receive matrix consists of a single plate-like acoustic receiver, with the result that acoustic beams transmitted by various, simultaneously activated acoustic transmission elements can be simultaneously detected.

In a further preferred embodiment yet in accordance with the invention, the device comprises an activatable generator for forming acoustic transmitters for transmitting focussed acoustic beams, said transmitters consisting of concentric circles of separate acoustic transmission elements and being displaceable in the row and the column direction.

Thus, in the acoustic transmission matrix acoustic transmitters are formed which consist of activated acoustic transmission elements which are arranged in concentric circles. By activation of all acoustic transmission elements of a circle in the suitable phases acoustic beams focussed in accordance with the Fresnel principle are produced. The body to be examined can thus be successively scanned by displacement of the circles in the direction of the rows. The plate-like acoustic receiver situated opposite the acoustic transmission matrix then detects the focussed acoustic beams. If the acoustic transmission matrix is large enough, the concentric circles of the acoustic transmitter can also be shifted in the direction of the matrix columns for the scanning of various layers of the body. A typical acoustic transmission matrix can consist of some thousands of columns and some hundreds of rows.

In a further preferred embodiment of the invention, the acoustic converter consists of acoustic transmission elements which serve to generate fan-shaped acoustic beams and which are situated one above the other in the direction of the axis of rotation, and of a two-dimensional acoustic receive matrix which is composed of separate acoustic receive elements and whose columns extend parallel to the axis of rotation and whose rows are at least partly curved around the axis of rotation.

The separate acoustic transmission elements which are arranged one above the other are successively activated to transmit fan-shaped acoustic beams. The acoustic receive elements each time situated opposite an acoustic transmission element can then be activated to measure the transit times and intensities of the individual acoustic beams, so that the body to be examined can be scanned in a three-dimensional zone each time for an angular position of acoustic converter, a suitable number of angular positions being chosen in this respect.

In another preferred embodiment of the invention, the acoustic receive elements of the acoustic converter are arranged in a ring-like manner and one above the other in the direction of the axis of rotation in order to form a hollow cylinder for accommodating the body to be examined, acoustic transmission rings formed similar to the acoustic receive rings being situated above and below the acoustic receive rings.

The acoustic transmission rings consist of acoustic transmission elements which are adjacently arranged in the circumferential direction and which can be separately activated. Using this acoustic converter, acoustic beams which are transmitted by an acoustic transmission element which is situated, for example, in the upper acoustic transmission ring, are received by a matrix column which is situated radially oppositely thereto and which consists of separately activated acoustic receive elements. Subsequently, an acoustic transmission element of the lower acoustic transmission ring which is situated below this matrix column is activated, the acoustic beams thereof reaching the acoustic receive elements situated radially oppositely thereto in order to be measured. Thus, a plane of the acoustic beams passing through the body is defined, said plane containing the axis of the hollow cylinder and being rotated each time by activation of given, radially oppositely arranged acoustic transmission elements in the upper and the lower acoustic transmission rings, so that the body can be fully scanned without mechanical rotation of the tank. The extent of the angular rotation is then dependent of the width of the individual acoustic transmission elements and receive elements.

In a further preferred embodiment in accordance with the invention, separate acoustic transmission elements are provided one above the other in the acoustic receive rings at a distance from each other in the circumferential direction, so that matrix columns of acoustic transmission elements are formed which are distributed over the circumference of the hollow cylinder. The matrix columns of the acoustic transmission elements are then radially oppositely situated. When activated, each acoustic transmission element can transmit, for example, a fan-shaped acoustic beam which is detected by a part of a matrix row which is situated at the same level and which consists of separate acoustic receive elements. Any acoustic transmission elements present in the matrix row can then be connected as acoustic receivers. If this is not possible, either the measuring values not present at this position are formed by interpolation of measuring values of adjacent acoustic receive elements or they are not taken into account. By activation of the separate acoustic transmission elements and acoustic receive elements in the circumferential direction and in the direction of the matrix column, respectively, the body is again irradiated in a three-dimensional zone for measuring the transit times and intensities of the acoustic beams. Mechanical rotation of the tank can again be omitted; however, mechanical displacement in the longitudinal direction of the axis of the hollow cylinder can be performed, for example, for adjustment of the tank.

In another embodiment of the invention, the acoustic converter consists of a single ring of adjacently situated acoustic receive elements wherebetween separate acoustic transmission elements are arranged at a distance from each other in the circumferential direction, the acoustic converter being displaceable in the direction of the axis of rotation.

It is thus achieved that the electronic equipment for activating separate acoustic transmission elements and acoustic receive elements can be reduced, so that the costs of manufacturing such a device are lower.

The invention will be described in detail hereinafter with reference to the accompanying diagrammatic drawings in which.

For the sake of simplicity the method will be described on the basis of the determination of a two-dimensional structure distribution (acoustic refractive index distribution). The method can be readily extended to three dimensions by also taking into account the third coordinate in the below equations.

Figure 1:
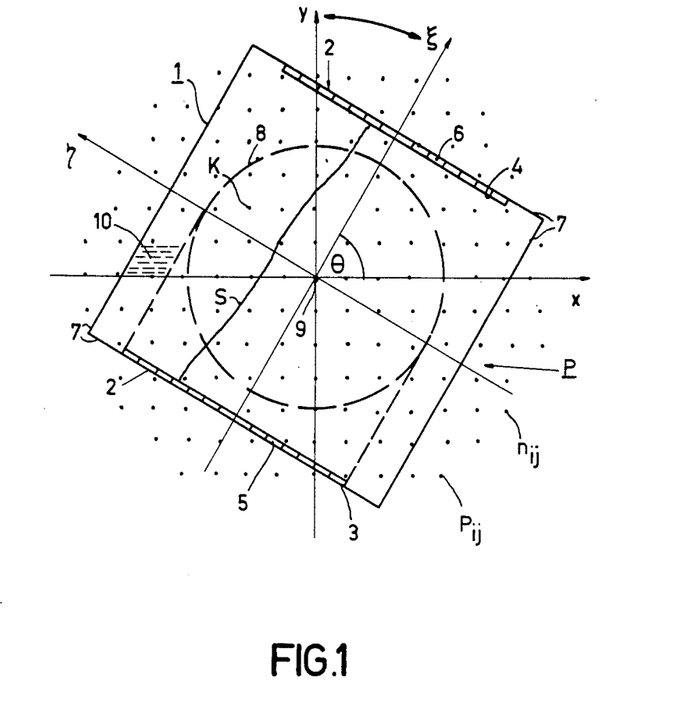
FIG. 1 is a plan view of a tank with a body to be examined and an associated point matrix.

FIG. 1 is a drawing for the description of the method. The figure concerns a plan view of a square tank 1 which accommodates an acoustic converter 2 which comprises two oppositely arranged matrices 3, 4, the former matrix (3) consisting of a row of acoustic transmission elements 5, while the latter matrix (4) consists of a row of acoustic receive elements 6.

Inside the tank 1, being permanently associated with a flat cartesian coordinate system whose axes $\xi$, $\eta$ extend perpendicularly to the sidewalls 7 of the tank, a body K to be examined is accommodated. It is surrounded by an acoustic coupling medium, for example, water; the flat extension of said body may be so large that it fills a maximum object circle 8 (denoted by broken lines) which is determined by the length of the matrix rows. The body K has permanently associated with it a flat point matrix P, the values $n_{ij}$ of the acoustic refractive indices being preselected at the points $P_{ij}$ thereof in agreement with the structure of the body K. The flat point matrix P is situated in the x-y plane of a cartesion coordinate system which is permanently associated therewith, the x-y plane and the $\xi$-$\eta$ plane and the origins of the coordinate systems (x-y) and ($\xi$, $\eta$) being coincident. Both coordinate systems, ($\xi$, $\eta$) and (x, y), can be rotated with respect to each other about an axis of rotation 9 which extends through their origins and perpendicularly to the $\xi$-$\eta$ plane.

The body can be successively irradiated by acoustic beams S (ultrasonic beams) from different directions by rotation of the tank 1 about the axis of rotation 9. The ultrasonic beams have a frequency of some MHz. For a direction which encloses an angle $\theta$ with the x-axis, the acoustic transmission elements 5 are successively activated to transmit acoustic beams S. The acoustic receive element 6 situated opposite the activated transmission element and/or one or more other receive elements are activated for the detection of the acoustic beams S, as desired.

From the measured transit times T of the acoustic beams S, the acoustic refractive index $n_{ij}$ at the matrix points $P_{ij}$ of the point matrix P is determined in accordance with a method to be described hereinafter. Furthermore, from the intensities I the distribution of the absorption coefficient $\alpha$ at the matrix points $P_{ij}$ can be determined if the distribution of the refractive indices $n_{ij}$ in the point matrix P is known.

If k is the number of an acoustic transmission element 5 and 1 is the number which indicates a given angle $\theta$, the formula below is applicable to the line integral of the acoustic refractive index, taking into account a correction term $\varepsilon_{kl}$ which is introduced by measuring inaccuracies and model assumptions (for example, that the geometric acoustics are applicable):

$$\int_{r_{kl}(n)} n \, ds + \varepsilon_{kl} = S_{kl} = w_o T_{kl} \tag{1}$$

Therein $w_o$ is the velocity of sound in water, $T_{kl}$ is the measured transit time of an acoustic beam S, and $r_{kl}(n)$ is the path travelled by the measured acoustic beam S. The index k then ranges from $k=1,\ldots,K$, K indicating the total number in acoustic transmission elements 5 of a matrix row. The index l ranges from $l=1,\ldots,L$, L indicating the total number of angles $\theta$.

The path $r_{kl}(n)$ is unknown, but can at least be approximated on the basis of the previously selected distribution of the acoustic refractive indices $n_{ij}$. To this end, the integration path ($r_{kl}(n)$) is subdivided into discrete path elements, so that the following is applicable:

$$\sum_{ij} a_{ij}^{kl}(\vec{n}) n_{ij} + \widetilde{\varepsilon}_{kl} = S_{kl} \tag{2}$$

Therein, $\vec{n}$ is the vector of the unknown $n_{ij}$, for example, $\vec{n} = (n_{11}, n_{12}, \ldots, n_{1n}, n_{21}, \ldots)$. The subdivision error as well as the correction factor kl is also included in the term $\widetilde{\varepsilon}_{kl}$. The coefficients $a_{ij}^{kl}(\vec{n})$, which are dependent on $\vec{n}$, can then be calculated in known manner (if $\vec{n}$ is known). To this end, interpolation of the refractive indices $n_{ij}$ which surround the path elements is used to calculate refractive indices $n_{ij}$ which are situated on the path elements of the integration path and which each time produce the desired coefficients $a_{ij}^{kl}(\vec{n})$ multiplied by the path elements.

The approximation of the radiation path (integration path) $r_{kl}(\vec{n})$ is necessary for calculating the coefficients $a_{ij}^{kl}(\vec{n})$. To this end, a given differential equation, i.e. the "beam equation" originating from the eikonal equation (see also "Computerized Tomographic Imaging using X-rays and Ultrasound, C. V. Jakowatz, A. C. Kak, TR-EE 76-26, July 1976, School of Electrical Engineering, Purdue University, West Lafayette, Ind. 47907)) is solved, taking into account the starting or boundary value problems. The approximative solution is possible if the vector $\vec{n}$ is known. The small disturbances $\widetilde{\varepsilon}_{kl}$ are neglected, and it is attempted to determine the acoustic refractive indices so that $$\sum a_{ij}^{kl}(\vec{n}) n_{ij} = w_o T_{kl} = S_{kl} \tag{3}$$

is at least approximately valid. A secondary condition is introduced in that $n_{ij} = 1$, if $n_{ij}$ is associated with a point $P_{ij}$ of the point matrix which is in the water 10.

For determining the refractive indices $n_{ij}$ of the body K, a sensible preselected refractive index distribution which approximates the structure of the body K is given in advance (vector $\vec{n}^o$). From this given distribution $\vec{n}^o$ the associated transit times $t_{kl}$ can be determined in accordance with the equation $$\sum_{ij} a_{ij}^{kl}(\vec{n}^o) n_{ij}^o = w_o t_{kl}, \tag{4}$$

which, however, generally do not correspond to the measured transit times $T_{kl}$. After measurement of the transit times $T_{kl}$ of the acoustic beams S in the various directions, all equations (3) are taken in a sensible sequence, for example, successively each time with a fixed index l and a variable index k and the values of the refractive indices $n_{ij}^o$ are modified so, that the calculated transit times $t_{kl}$ correspond to the measured transit times $T_{kl}$. This is realized by determination of the correction factor $A_{kl}$ in accordance with $$A_{kl} = ((S_{kl} - \sum_{ij} a_{ij}^{kl}(\vec{n}^q) n_{ij}^q) / \\ ((\sum_{ij} (a_{ij}^{kl}(\vec{n}^q))^2)) \tag{5}$$

Thus, the vector $\vec{n}^q$ (for example, with $q=0$, first approximation) is corrected by correction values $\vec{A}$ so that $$n_{ij}^{q+1} = n_{ij}^q + \overline{A} = n_{ij}^q + C_{ij}^q \cdot A_{kl} \cdot a_{ij}^{kl}(\vec{n}^q) \tag{6}$$

Therein, the index q indicates the number of iteration steps, while $C_{ij}^{kl}$ is a suitably chosen attenuation parameter with $0 < C_{ij}^{kl} \leq 1$ for generating convergence. The values $n_{ij}^{q+1}$ thus calculated can be smoothed, if desired, to a given extent for improvement of the reconstruction quality by forming the weighted mean value of the surrounding refractive indices. The iteration process is stopped when all equations (3) have been sufficiently satisfied, i.e. when the difference between the measured transit time $T_{kl}$ and the calculated transit time $t_{kl}$ is sufficiently small for all acoustic beams S, or after a fixed number of iteration steps.

Equations (1 to 6) are extended to three dimensions. Unknown values from different layers defined by the detector device 2 then occur in each equation. The reconstruction quality, however, is additionally improved because the three-dimensional course of the acoustic beams S is completely taken into account.

In practice it may occur that given measuring values are not present, for example, because bones excessively attenuate the ultrasonic signal (acoustic beam). In such a case, the relevant equation can be omitted for the reconstruction, without the reconstruction quality being essentially affected.

The reconstruction of the absorption coefficient $\vec{\alpha} = (\alpha_{11}, \alpha_{12}, \ldots)$ is performed following the determination of the refractive index distribution. For determining a two-dimensional distribution of the absorption coefficient, the following equation is applicable $$\int_{r_{kl}(n)} \alpha \, ds = B_{kl} = \ln\left(\frac{I_{kl}^o}{I_{kl}}\right) \tag{7}$$

Therein, the absorption signals $B_{kl}$ are known. Because the beam path $r_{kl}(n)$ is known from the preceding refractive index reconstruction, $I_{kl}^o$, i.e. the transmitted acoustic intensity, can be determined for a known transmission characteristic of an acoustic transmission element 5 in the direction of each radiation path $r_{kl}(n)$). The intensity $I_{kl}$ is measured each time by acoustic receive elements 6. Instead of the intensities $I_{kl}$, $I_{kl}^o$, the maximum amplitudes $A_{kl}^{max}$ and $A_{kl}^{omax}$ can also be measured and calculated, respectively.

The radiation path $r_{kl}(n)$ is again subdivided into discrete path elements, so that the total absorption along a radiation path S can be described by the equation $$\sum_{ij} a_{ij}^{kl}(\vec{n}) \alpha_{ij} + \tilde{\tilde{\epsilon}}_{kl} = B_{kl} \qquad (8)$$

in which $k=1, \ldots K$ and $l=1, \ldots, L$. The error $\tilde{\tilde{\epsilon}}_{kl}$ introduced by the subdivision is neglected and the values $a_{ij}^{kl}(\vec{n})$ are coefficients describing the radiation path $r_{kl}(n)$. These are the same coefficients which have already been calculated for the preceding refractive index reconstruction.

The distribution of the acoustic absorption coefficient $\alpha_{ij}$ at the individual points $p_{ij}$ of the point matrix P can be determined in the manner used for determining the refractive index distribution. A given acoustic absorption coefficient distribution is assumed in advance on the points $P_{ij}$. From this assumed distribution of the absorption coefficient $\vec{\alpha}^o$ (q=0), the total absorption $b_{kl}$ associated with an acoustic beam can be calculated in accordance with the equation $$\sum_{ij} a_{ij}^{kl}(\vec{n}) \alpha_{ij}^o = b_{kl}, \qquad (9)$$

This value generally does not correspond to the measured absorption signal $B_{kl}$. All equations (8) are then successively taken in a sensible sequence, after determination of the individual absorption signals $B_{kl}$, and $\alpha_{ij}^q$ is modified so that the total absorption $b_{kl}$ each time corresponds to the measured absorption signal $B_{kl}$. This is realized by determination of a correction factor $\beta_{kl}$ with $$\beta_{kl} = (B_{kl} - \sum_{ij} a_{ij}^{kl}(\vec{n}^q) \alpha_{ij}^q) / \left(\sum_{ij} (a_{ij}^{kl}(n^q))^2\right) \qquad (10)$$

Thus, the absorption distribution $\vec{\alpha}^q$ is corrected by correction values $\overline{B}$ so that for all ij $$\alpha_{ij}^{q+1} = \alpha_{ij}^q + \overline{B} \qquad (11)$$

The index q is again a counting index of the iteration, while the the correction quantity $\overline{B}$:

$$\overline{B} = \beta_{kl} a_{ij}^{kl}(\vec{n}^q) \qquad (12)$$

Obviously, this method can also be readily extended to three dimensions in that the corresponding third coordinate is added to each equation (7 to 12). The disturbances caused by reflections of the acoustic beams S can be eliminated in known manner by measurement at two different sound frequencies.

Figure 2:
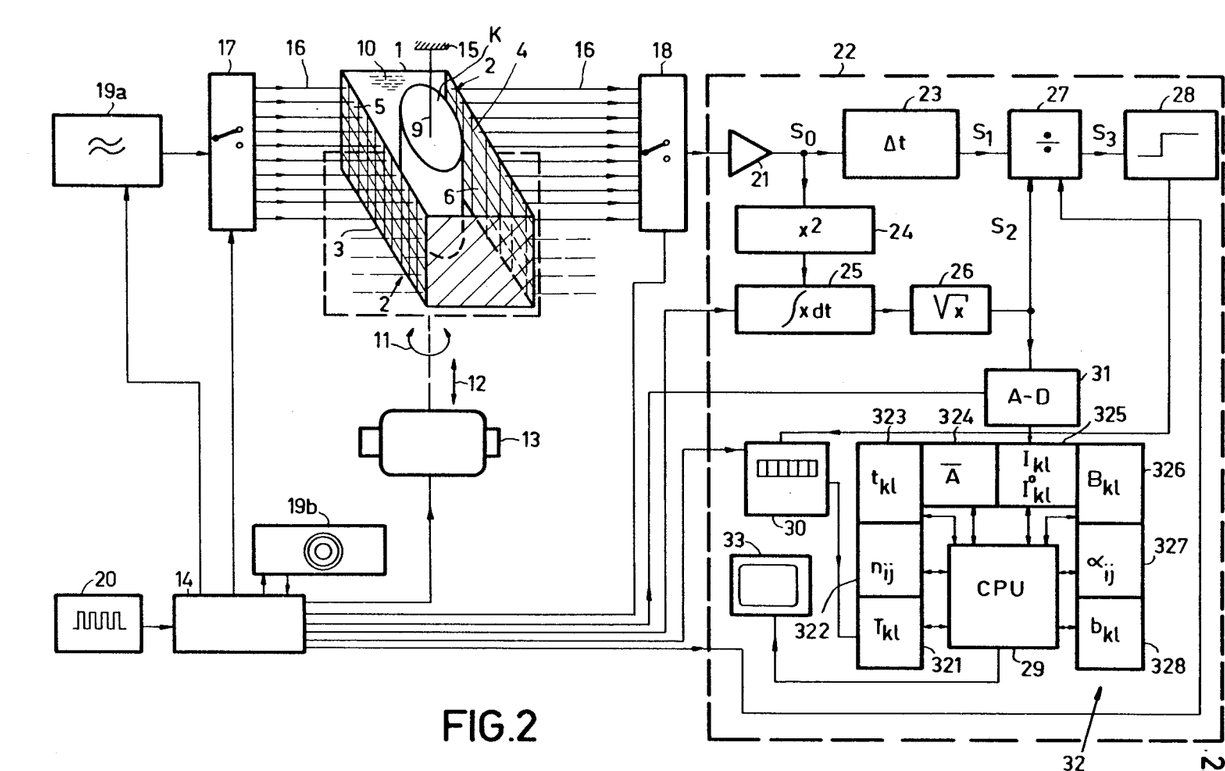
FIG. 2 is an embodiment of a device for performing the method in accordance with the invention.

FIG. 2 diagrammatically shows the device for performing the method. The tank 1 has a rectangular shape and accommodates a body K which is surrounded by an acoustic coupling medium 10, for example water, and which is introduced into the tank 1 from the top. The acoustic converter 2, is arranged on two opposite walls inside the tank 1 and consists of an acoustic transmission matrix 3 and an acoustic receive matrix 4 the matrices comprise separate acoustic transmission elements 5 and acoustic receive element 6, respectively, which are arranged in rows and columns and which comprise, for example, a flat, a square transmission surface and receive surface, respectively. The transmission surfaces and receive surfaces, obviously, may also have a different, suitable geometry. For example, the transmission surfaces and receive surfaces of the acoustic transmission elements and the acoustic receive elements, respectively, may be concave. Furthermore, the tank 1 is mechanically rotatable about an axis of rotation 9 and displaceable in the longitudinal direction of the axis of rotation 9. This is realized by means of a suitable motor 13 which is controlled by a control unit 14. Obviously, the body K must be maintained in the correct position by suitable a enchoring 15 during rotation of the tank 1. During examination of a human body, for example, a female breast, the tank 1 is arranged underneath an examination table (not shown) so that the breast can be introduced into the tank 1 when the patient lies down on the table. The acoustic converter 2 need not necessarily be arranged against the inner walls 7 (FIG. 1) of the tank 1. The acoustic transmission matrix 3 and the acoustic receive matrix 4 can also be arranged further inside in the tank, parallel with respect to each other and opposite each other. They can also be arranged in a leakproof and slidable manner in openings (not shown) in the tank 1.

Each acoustic transmission element 5 and each acoustic receive element 6 is connected, via an electrical connection lead 16, to an electronic switch 17 and 18, respectively, which is controlled by the control unit 14. The control unit 14 itself is controlled by a clock generator 20. The electronic switch 17 successively connects each acoustic transmission element 5 to a high frequency generator 19a for generating ultrasonic pulses. The ultrasonic frequency maybe a few megahertz.

Simultaneously with the activation of an acoustic transmission element 5, an acoustic receive element 6 which is for example, situated directly opposite the former element can be activated by means of the electronic switch 18 so that, for each transmitted ultrasonic pulse, an ultrasonic pulse is received. The body K can thus be scanned one line after the other. Obviously, acoustic receive elements 6 other than the one situated directly opposite the acoustic transmission element 5 can be activated for detection of one or more ultrasonic pulses.

The acoustic beams (ultrasonic pulses) detected by the separate acoustic receive elements 6 are directly converted into electrical signals which pass through the electronic switch 18 and a subsequent amplifier 22 which forms part of an electronic device 21. Preferably, for each data channel or for each acoustic receive element 6 there is provided such an amplifier 21, possibly in combination with further electronic stages yet to be described hereinafter.

The analog output signal $S_0$ of the amplifier 21, corresponding to the ultrasonic pulse, is applied to a delay member 23 and also to a squaring circuit 24 which squares the amplitude of each output signal $S_0$. Subsequently, the squared output signal is integrated by means of an integrator 25, after which the root is extracted by means of a root extractor circuit 26. On the output of the root extractor circuit 26 a signal $S_2$ (the root of the mean squared signal of the received ultrasonic pulse) is available which corresponds to the measured intensity $I_{kl}$ of the ultrasonic pulse. This signal $S_2$ is divided by the delayed output signal $S_1$ of the amplifier 21 in a divider 27 in order to generate a normalized signal $S_3$ which is applied to a threshold discriminator 28 for measuring the transit time of the ultrasonic pulse. The object of this operation is to normalize the amplitude of the output signal $S_0$ in order to obtain a transit time which is independent of the amplitude. The constant delay introduced by the delay line 23 can be subtracted at a later stage in a digital CPU 29. The integrator 25, of course, must be reset before the arrival of a new output signal $S_0$. The divider 27 may be switched on only some time after the beginning of the integration in order to prevent, for example, the dividing by zero of a noise signal present, so that it exceeds the threshold of the threshold discriminator 28. The foregoing is controlled by the control unit 14.

A counter 30 is reset by the control unit 14 each time an ultrasonic pulse is transmitted, after which it starts to count. Counting stops when the threshold in the threshold discriminator 28 is exceeded by the amplitude of the normalized signal $S_3$; the transit time $T_{kl}$ of the ultrasonic pulse is thus measured. This measured transit time $T_{kl}$ is stored in a first section 321 of a memory 32.

The memory 32 furthermore comprises a second section 322 for the storage of the values $n_{ij}$ of the acoustic refractive indices, preselected or adapted on the basis of the measuring results, a third section 323 for storing the calculated values $t_{kl}$ of the transit times, and a fourth section 324 for the storage of further data such as the correction data $\overline{A}$ and other data temporarily required for the calculations. A central processor unit 29 is adapted to perform all calculations described with reference to FIG. 1.

In order to determine the distribution of the absorption coefficient $\alpha$, the signal $S_2$ which corresponds to the measuring intensity $I_{kl}$ is applied to an analog-to-digital converter 31 and is stored in a fifth memory section 325 which also receives the associated intensity $I_{kl}^0$ of the transmitted acoustic beam. Therefrom, the central processor unit 29 calculates the absorption signal $B_{kl}$ for each beam path S, the value of said signal being stored in a sixth memory section 326. The values $\alpha_{ij}$ of the absorption coefficients, preselected or adapted on the basis of the measuring results, are stored in a seventh memory section 327, and the value of the calculated absorption $b_{kl}$ along each radiation path S is stored in an eighth memory section 328.

Using these data, the central processor unit 29 reconstructs an image of the body K which is made visible via a display device 33, for example, a display screen or a printer.

Figure 3:
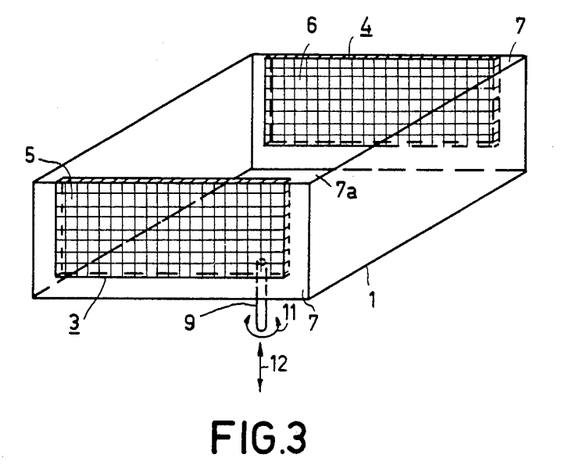
FIGS. 3 to 11 are different embodiments of tanks for a device in accordance with the invention.

FIG. 3 shows a rectangular tank 1 in which an acoustic transmission matrix 3 and an acoustic receive matrix 4 are arranged on opposite walls 7. The tank 1 comprises a rotary shaft 9 which is connected to its bottom 7a and around which the tank is rotatable. Displacement in the longitudinal direction of the rotary shaft is also possible. The electrical connection leads 16 (FIG. 2) to the individual acoustic transmission elements 5 and the acoustic receive elements 6 have been omitted for the sake of clarity. The acoustic transmission matrix and the acoustic receive matrix 4, being arranged against the inner side of the tank walls 7, consists of from 64 to 128 columns and 10 rows. Obviously, the numbers of columns and rows can be increased or decreased in accordance with the object dimensions and the object construction or with the required resolution. The starting position and the end position of the acoustic beams are determined by this construction of the acoustic converter 2.

Figure 4:
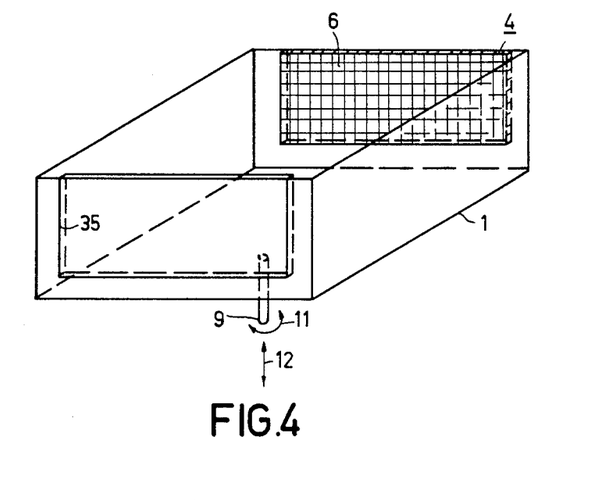

In FIG. 4, the acoustic transmission matrix 3 (FIG. 3) arranged in the tank 1 is constructed as a plate-shaped acoustic transmitter 35, while the acoustic receive matrix 4 consists of separate acoustic recieve elements 6. Activation of the plate-shaped acoustic transmitter 35 produces approximately flat acoustic wave fronts, so that the starting direction of the acoustic beams which extend perpendicularly to the acoustic wave fronts is known. Therefore, simultaneous measurements by all active acoustic receive elements 6 is possible, the end position of the acoustic beams being defined. The acoustic receive matrix consists of from 64 to 128 columns and 10 rows.

Figure 5:
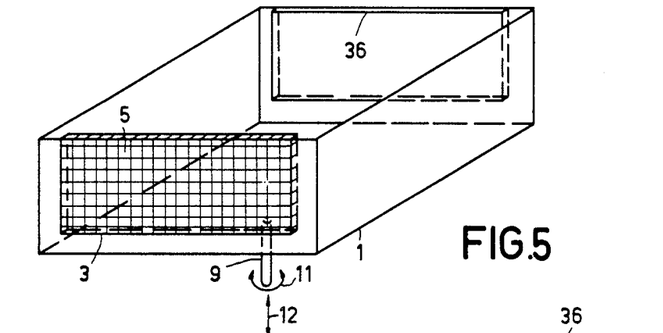

FIG. 5 shows a tank 1 which accommodates an acoustic transmission matrix 3 which consists of separate acoustic transmission elements 5, and a single plate-shaped acoustic receiver 36. The separate acoustic transmission elements 5 are successively activated, for example, successively in a matrix row, the matrix rows being successively activated. The starting position and the starting direction of the acoustic beams are thus defined. The acoustic transmission matrix may consist of, for example, from 68 to 124 columns and 10 rows.

Alternatively, the acoustic transmission matrix 3 may consist of a few thousands of columns and a few hundreds of rows. the resolution, and hence the quality of the reconstructed acoustic images, is thus improved. Moreover, using a further generator 19b, via the control unit 14 and the electronic switch 17 concentric circles (not shown) of activated acoustic transmission elements 5 can be selected for focussing the ultrasonic beams, the individual concentric rings then being activated to generate ultrasonic beams by suitably phase-shifted electric signals. The complete body K can then be scanned by displacement of the circle in the row or column direction. The principle of this procedure is extensively described in published Netherlands Patent Application No. 7809905.

Figure 6:
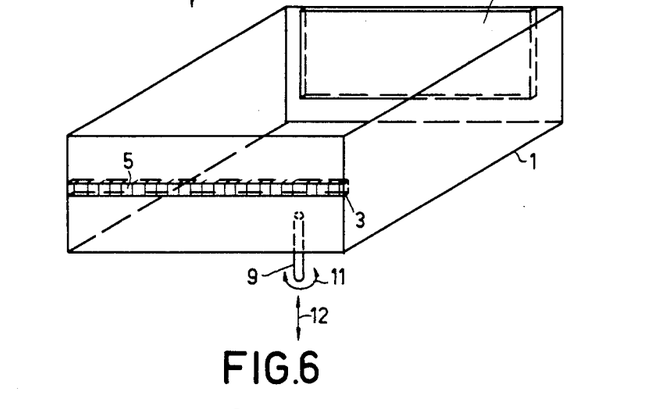

The tank 1 shown in FIG. 6 comprises an acoustic transmission matrix consisting of only a single row. The individual acoustic transmission elements 5 are successively activated to generate ultrasonic pulses which reach an oppositely situated plate-shaped acoustic receiver 36.

Figure 7:
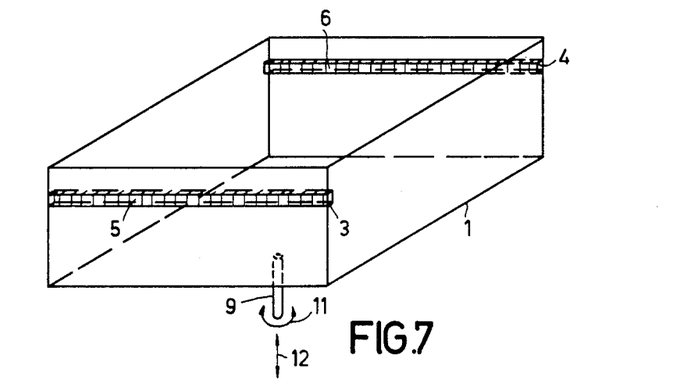

In FIG. 7, the acoustic transmission matrix 3 and the acoustic receive matrix 4 each consists of only a single matrix row, each time one or more acoustic receive elements being capable of detecting the ultrasonic pulses when an acoustic transmission element 5 is activated. Both matrix rows are situated at the same level. By displacement of the tank 1 in the longitudinal direction of the rotary shaft 9 (arrow 12), different layers of the body K (not shown) can be reconstructed. The acoustic transmission elements 5 transmit defocused ultrasonic beams, so that the acoustic receive elements 6 detect ultrasonic beams in any case.

Figure 8:
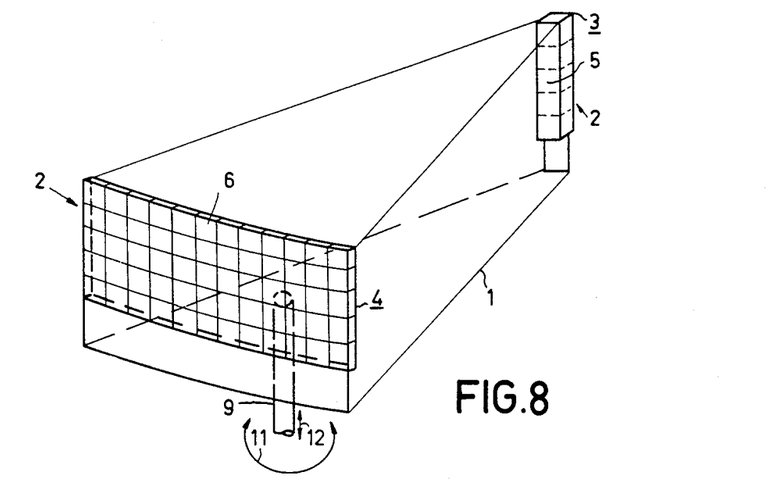

FIG. 8 shows an acoustic converter 2 whose acoustic transmission matrix 3 consists of a matrix column with individual acoustic transmission elements 5, while the acoustic receive matrix 4 consists of a number of acoustic receive elements 6 which are arranged in rows and columns, the rows being curved. The acoustic receive matrix 4 consists of from 64 to 128 columns and 10 rows. The entire tank 1 is wedge-shaped and can be rotated around the rotary shaft 9 (arrow 11) and displaced in its longitudinal direction (arrow 12). When an acoustic transmission element 5 is activated, all acoustic receive elements 6 can be activated each time for an angular position of the tank 1, so that the scanning time of a body K is substantially reduced.

Figure 9:
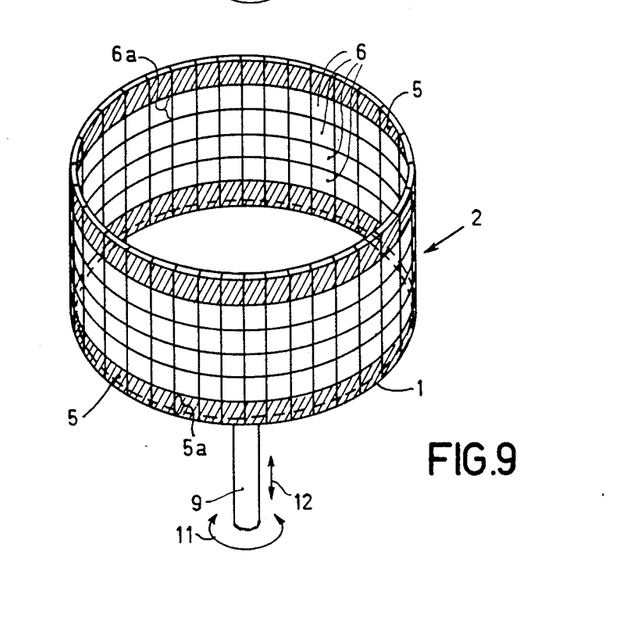

The tank 1 shown in FIG. 9 is constructed as a hollow cylinder. On its inner side there is provided an annular acoustic converter 2 which comprises a number of rings 6a, situated one above the other, of adjacently arranged acoustic receive elements 6. Above and below the acoustic receive rings 6a there are provided acoustic transmission rings 5a which consist of adjacently arranged acoustic transmission elements 5. The tank 1 is rotatable around its symmetry axis (rotary shaft 9) and is displaceable in the longitudinal direction of the rotary shaft 9. The direction of the acoustic beam S can be changed without mechanical rotation of the tank 1 by suitable activation of individual acoustic transmission elements 5 which transmit fan-shaped or lobar ultrasonic beams. Therefore, the tank 1 can also be arranged on given bodies or parts of a body if it is ensured that the acoustic coupling medium cannot escape from the tank 1 and at the same time contacts the body K (not shown). To this end, the tank 1 can be provided with a deformable elastic foil, an acoustic coupling medium being present between the foil, which contacts the body, and the acoustic converter 2. Examinations of the mammae can then be performed on a patient in the upright position.

Figure 10:
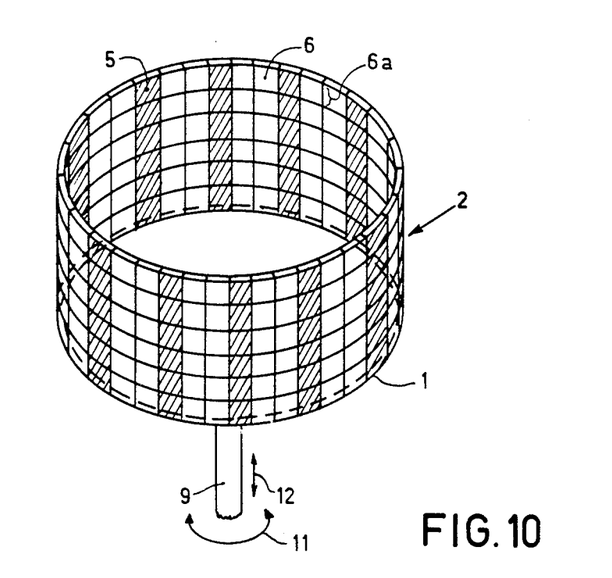

FIG. 10 shows a tank 1 in the form of a hollow cylinder, the inner side of which accommodates several acoustic receive rings 6a which are arranged one above the other and each of which consists of a number of acoustic receive elements 6 wherebetween separate acoustic transmission elements 5 are situated at regular distances. Thus, columns of acoustic transmission elements 5 and acoustic receive elements 6 are formed in the longitudinal direction of the rotary shaft 9 (symmetry axis). In FIG. 10 only two columns of acoustic receive elements 6 are shown between each two columns of acoustic transmission elements. Actually, a substantially larger number of columns of acoustic receive elements 6 are situated between every two columns of acoustic transmission elements 5. It is not necessary to rotate or displace the tank 1, because the acoustic transmission elements 5 and the acoustic receive elements 6 can be suitably activated. The separate acoustic transmission elements 5 (for example, piezoelectric transducers) transmit fan-shaped or lobar acoustic beams which reach different, oppositely situated acoustic receive elements 6.

Figure 11:
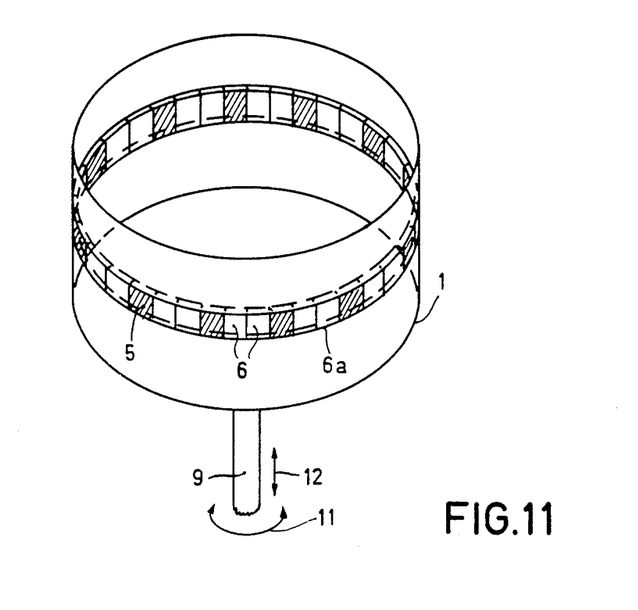

FIG. 11 shows a simpler embodiment of the tank 1 shown in FIG. 10. The iner wall of this embodiment accommodates only a single acoustic receive ring 6a, separate acoustic transmission elements 5 being provided between the acoustic receive elements 6 at a distance from each other in the circumferential direction. This tank 1, or the body K (not shown), must be displaced in the direction of the rotary shaft 9 (symmetry axis) for examination of different body layers. However, rotation of the tank 1 can again be dispensed with.

What is claimed is:

1. In a method for determining the internal structure of a body comprising the steps of:
    passing a plurality of acoustic beams through a body in different directions from one or more acoustic transmission elements to one or more separate acoustic reception elements; measuring the value of the transit time of each of said beams through the body; and utilizing the measured transit time values to calculate the value of the acoustic refractive index at points in a matrix associated with the body; the improvement comprising the steps of:
    first assuming a distribution of acoustic refractive index values at preselected points in the matrix, which approximate known body structure, said assumed distribution taking into account the geometry of the transmission and reception elements;
    using said assumed distribution to calculate the path of each of said beams throught the body;
    calculating an assumed transit time for each beam along the determined paths; and
    then comparing the assumed transit time with the measured value of the transit time to generate stepwise corrections for the calculated value of the acoustic refractive index at points in the matrix.

2. The method of claim 1 wherein the assumed distribution of acoustic refractive index values is smoothed by forming a weighted mean value of neighboring acoustic refractive index values at points in the matrix.

3. A method as claimed in claim 1 further comprising the steps of:
    measuring the intensity of the acoustic beams received by the reception elements;
    utilizing the measured intensity to calculate the total absorption value for each of said beams;
    determining a distribution of absorption coefficient values at points in the matrix from the calculated total absorption values;
    calculating an assumed absorption value for each beam along the determined paths; and
    then comparing the assumed absorption values with the calculated absorption values to generate stepwise corrections for the calculated value of the absorption coefficient at points in the matrix.

4. The method of any of claim 1 through 3 wherein the direction of the beams is changed by rotating the acoustic transmission elements and acoustic reception elements around a fixed axis.

5. The method of any of claim 1 through 3 wherein the direction of the acoustic beams is changed by activation of separate acoustic transmission elements and acoustic reception elements which are distributed around the body and whose position remains unchanged with respect to the body.

6. In a device for determining the internal structure of a body of the type comprising: an acoustic converter disposed around the body which includes separate acoustic transmission elements and acoustic reception elements; means for selectively activating the transmission and reception elements for the transmission and reception, respectively, of acoustic beams; means for measuring the value of the transit time of the acoustic beams between the transmission elements and the reception elements; and means for calculating the acoustic refractive index at points in a matrix which is associated with the body from the measure values of the transit time; the improvement comprising:
    means for determining the paths of the acoustic beams through the body on the basis of an assumed distribution of the values of the acoustic refractive index in the body and for determining theoretical transit time values for acoustic beams following those determined paths; and
    means for comparing the measured transit time values with the theoretical transit time values and for correcting the calculated values of the acoustic refractive index at points in the matrix on the basis of the results of the comparison.

7. The device of claim 6 further comprising:
means for measuring the values of the intensity of acoustic beams received at the reception elements;
means for calculating absorption coefficients at points in the matrix on the basis of the measured intensity; and
means for calculating theoretical absorption values for the acoustic beams along the assumed beam paths, for comparing the calculated absorption values with the measured absorption values, and for correcting the calculated values of the absorption coefficients on the basis of the results of the comparison.

8. The device of claim 6 or 7 further comprising a tank which is rotatable about an axis and displaceable in the direction of the axis and wherein the acoustic converter comprises a flat acoustic matrix of transmission elements and a flat acoustic matrix of reception elements, said elements extending in columns and rows which are parallel and perpendicular, respectively, to the axis.

9. The device of claim 8 wherein the acoustic transmission element matrix comprises a single plate-shaped acoustic transmitter.

10. The device of claim 8 wherein the reception element matrix comprises a single plate-shaped acoustic receiver.

11. The device as claimed in claim 10 further comprising means for transmitting the acoustic beams from the acoustic transmission elements as focused acoustic beams by activating concentric circles of separate acoustic transmission elements and by displacing said circles along the rows and columns of the transmission element matrix.

12. The device as claimed in claim 8 wherein the acoustic receive matrix comprises a single plate-shaped acoustic receiver and the acoustic transmission element matrix comprises a row of several acoustic transmission elements.

13. A device as claimed in claim 8 wherein the acoustic transmission element matrix and the reception element matrix comprise a row of individual acoustic transmission elements and acoustic reception elements, respectively, said rows being displaceable in the direction of the axis.

14. A device as claimed in claims 6 or 7 comprising a tank which is rotatable around an axis and displaceable in the direction of the axis wherein the acoustic converter comprises a row of acoustic transmission elements, which are situated one above the other along the direction of the axis and which generate fan-shaped acoustic beams, and a two-dimensional matrix of acoustic reception elements having columns of elements which extend parallel to the direction of the axis and rows of elements which are at least partially curved around the axis.

15. A device as claimed in claim 6 or 7 comprising a tank which is rotatable around an axis and which is displaceable in the direction of the axis wherein the acoustic reception elements are disposed in a ring-like manner around the axis and are situated one above the other in the direction of the axis to form a hollow cylinder which surrounds the body to be examined and wherein the acoustic transmission elements are disposed in rings situated above and below the rings of acoustic reception elements.

16. A device as claimed in claim 15 wherein the acoustic transmission elements are situated within the ring of acoustic reception elements.

17. A device as claimed in claim 16 wherein the acoustic converter comprises a single ring of adjacently situated acoustic reception elements and separate acoustic transmission elements which are disposed between the reception elements and at a distance from each other, the acoustic converter being displaceable in the direction of the axis.

* * * * *